(12) United States Patent
Kim et al.

(10) Patent No.: US 12,002,620 B2
(45) Date of Patent: Jun. 4, 2024

(54) BED-INTEGRATED ELECTROMAGNETIC FIELD APPARATUS FOR CONTROLLING MOVEMENT OF MICROROBOT AND METHOD FOR DRIVING MICROROBOT BY USING SAME

(71) Applicant: KOREA INSTITUTE OF MEDICAL MICROROBOTICS, Gwangju (KR)

(72) Inventors: Jayoung Kim, Daejeon (KR); Jong Oh Park, Gyeonggi-do (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 707 days.

(21) Appl. No.: 17/273,794

(22) PCT Filed: Oct. 27, 2020

(86) PCT No.: PCT/KR2020/014714
§ 371 (c)(1),
(2) Date: Mar. 5, 2021

(87) PCT Pub. No.: WO2022/010044
PCT Pub. Date: Jan. 13, 2022

(65) Prior Publication Data
US 2022/0199309 A1    Jun. 23, 2022

(30) Foreign Application Priority Data

Jul. 7, 2020 (KR) .......................... 10-2020-0083576

(51) Int. Cl.
*H01F 7/20* (2006.01)
*A47C 21/04* (2006.01)
(Continued)

(52) U.S. Cl.
CPC ............. *H01F 7/20* (2013.01); *A47C 21/042* (2013.01); *A47C 31/003* (2013.01); *H01F 27/24* (2013.01);
(Continued)

(58) Field of Classification Search
CPC . H01F 7/20; H01F 27/24; H01F 27/28; H01F 27/306; A47C 21/042;
(Continued)

(56) References Cited

U.S. PATENT DOCUMENTS

2016/0189845 A1* 6/2016 Ito .......................... H02K 9/227
                                                          335/300
2018/0111319 A1* 4/2018 Brezoczky ............ B29C 64/255

FOREIGN PATENT DOCUMENTS

| CN | 101035484 A | 9/2007 |
|---|---|---|
| JP | 2007-054143 A | 3/2007 |

(Continued)

OTHER PUBLICATIONS

Office Action from corresponding Korean Patent Application No. 10-2020-0083576, dated Sep. 28, 2021.
(Continued)

*Primary Examiner* — Behrang Badii
*Assistant Examiner* — Jay Khandpur
(74) *Attorney, Agent, or Firm* — Harness, Dickey & Pierce, P.L.C.

(57) ABSTRACT

The present disclosure relates to a bed-integrated electromagnetic field apparatus for controlling movement of a microrobot, and a method for driving a microrobot by using the same. A bed-integrated electromagnetic field apparatus according to the present disclosure can accurately control the movement of a medical device that can be inserted into a human body, such as a microrobot, and enables reduction of the size of the apparatus so as to be used in a medical (Continued)

procedure for diagnosis and treatment of vascular disease and the like.

13 Claims, 12 Drawing Sheets

(51) Int. Cl.
    *A47C 31/00*     (2006.01)
    *A61B 34/00*     (2016.01)
    *A61B 34/30*     (2016.01)
    *H01F 27/24*     (2006.01)
    *H01F 27/28*     (2006.01)
    *H01F 27/30*     (2006.01)

(52) U.S. Cl.
    CPC ........... *H01F 27/28* (2013.01); *H01F 27/306* (2013.01); *A61B 34/30* (2016.02); *A61B 2034/301* (2016.02); *A61B 34/72* (2016.02); *A61B 2034/733* (2016.02)

(58) Field of Classification Search
    CPC . A47C 31/003; A61B 34/30; A61B 2034/301; A61B 34/72; A61B 2034/733
    See application file for complete search history.

(56) References Cited

FOREIGN PATENT DOCUMENTS

| KR | 10-2000-0022564 A | 4/2000 |
| KR | 10-2007-0041555 A | 4/2007 |
| KR | 10-2018-0129394 A | 12/2018 |
| KR | 10-1983648 B1 | 9/2019 |

OTHER PUBLICATIONS

International Search Report from corresponding PCT Application No. PCT/KR2020/014714, issued on Apr. 1, 2021.

* cited by examiner

BED-INTEGRATED ELECTROMAGNETIC FIELD APPARATUS FOR CONTROLLING MOVEMENT OF MICROROBOT AND METHOD FOR DRIVING MICROROBOT BY USING SAME

CROSS-REFERENCE TO RELATED APPLICATIONS

This application is a national phase application of PCT Application No. PCT/KR2020/014714, filed on Oct. 27, 2020, which claims priority to Korean Patent Application No. 10-2020-0083576, filed on Jul. 7, 2020. The entire disclosures of the applications identified in this paragraph are incorporated herein by references.

TECHNICAL FIELD

The present disclosure relates to a bed-integrated electromagnetic field apparatus and a method for driving a microrobot by using the same and, more specifically, to an electromagnetic field apparatus which can accurately control the movement of a microrobot, and which can be made compact and thus has excellent compatibility with other medical equipment.

BACKGROUND ART

A surgery using a microrobot (for example, a minimally invasive surgery) can precisely target the disease and can minimize the incision area, thereby reducing the patient's pain, and can shorten the recovery period. Therefore, extensive research has recently been conducted in connection with this surgical method.

Methods for controlling the movement of a microrobot may be classified into an external driving type and a self-driving type. The self-driving type includes a method of using, for propulsion, the pressure of a gas caused by a chemical interaction between an external fluid and the robot body, a method of using biological propulsion such as bacteria movements, and the like. However, the self-driving type has a problem in that the same is difficult to be applied inside a human body due to the low degree of freedom regarding control, the low degree of control precision, and chemical/biological toxicity issue, which are necessary for microrobot driving.

Methods for driving a microrobot by using a magnetic field are typical external driving methods that are highly safe inside human bodies, and may be divided into a method using a permanent magnet and a method using an electromagnetic driving coil device. Particularly, the method using an electromagnetic driving coil to control a microrobot, compared with the method using a permanent magnet, can precisely control the intensity and direction of the magnetic field by controlling the electric current applied to the coil. This merit diversifies the range of application, and the most extensive research has thus been conducted regarding this type. More particularly, research has been concentrated on propulsion of microrobots by using external magnetic fields, or on driving for treatment. Most research has been conducted on a two-dimensional plane, or to enable a simple movement in a three-dimensional space. A part or all of a medical device is made of a magnetic substance, without a battery or a separate driver, such that the electromagnetic field driving coil device can be controlled by using a magnetic field.

A medical device driven by using an electromagnet in this manner can be controlled by a magnetic field produced by applying an electric current to a coil fixedly disposed on the outside. By controlling the intensity, direction, and the like of the electric current applied to each coil, the medical device can be driven as desired. Methods using an electromagnet can be controlled more easily than methods using a permanent magnet, and the movement of the medical device can be quickly controlled according to the characteristics of the coil.

However, such conventional driving devices employ a large number of electromagnets and thus has multiple drawbacks in connection with operating the same. Specifically, a conventional electromagnetic field driving device uses multiple electromagnets to drive a microrobot, thereby making the device bulky. It thus becomes inefficient to use and operate the device in the surgery space. In addition, the large number of electromagnets increases the number of power supplies and the necessary output, thereby posing the problem of huge power consumption. There are also restrictions regarding the size of a conventional electromagnetic field driving device and the direction in which (electro)magnets are arranged. This degrades the compatibility with equipment used in other medical facilities (for example, X-ray devices).

In addition, conventional electromagnetic field driving devices using permanent magnets generally control wired microrobots by using two permanent magnets. However, it is difficult to control robots in directions other than the direction in which magnets are arranged. Furthermore, a control space for permanent magnets is secured by using a motor, but there is a problem in that it is difficult to control the magnetic field in real time due to a time difference in motor movement.

Therefore, there is a need for an electromagnetic field driving device which can accurately control the movement of a wired or wireless microrobot, which has a minimized number of electromagnets and thus can make the device compact, and which has excellent compatibility with medical equipment.

SUMMARY

Technical Problem

Accordingly, the present inventors manufactured a bed-integrated electromagnetic field apparatus including a bed, a first electromagnet disposed inside the bed, and a second electromagnet disposed to form a predetermined angle with the first electromagnet, and confirmed that the apparatus according to the present disclosure has excellent accuracy and precision in connection with microrobot driving.

Therefore, it is an aspect of the present disclosure to provide a bed-integrated electromagnetic field apparatus.

It is another aspect of the present disclosure to provide a microrobot driving method.

Technical Solution

The present disclosure relates to a bed-integrated electromagnetic field apparatus for the controlling the movement of a microrobot, and a method for driving a microrobot by using the same. The electromagnetic field apparatus according to the present disclosure is advantageous in that the same can accurately control the movement of a microrobot, and the apparatus can be made compact and thus has excellent compatibility with other medical equipment.

The present inventors confirmed that, by accurately configuring an electromagnetic field area for driving a microrobot, the microrobot can be precisely moved.

Hereinafter, the present disclosure will be described in more detail.

As used herein, the term "medical device that can be inserted into a human body" refers to any medical device that can be inserted into a human body, a part or all of which is designed surgically/medically, and encompasses a medical device that can remain inserted into a human body, after a surgery, to maintain life, and a medical device that can be temporarily inserted into a human body for the purpose of surgery or diagnosis. Particularly, the medical device that can be inserted into a human body according to the present disclosure includes a magnetic substance that is magnetized inside a magnetic field, and a permanent magnet, for example, may be used as the magnetic substance.

As used herein, the term "microrobot" refers to a type of medical device that can be inserted into a human body. Microrobots may be classified into mechanical/mechanical microrobots including a permanent magnet or soft ferrite as a millimeter-scaled magnetic substance (for example, a blood vessel robot or an active capsule endoscope), high-molecular/cell-based microrobots including magnetic nanoparticles as micro/nano-scaled magnetic substances (for example, microcarriers for DDS, micro-scaffolds for delivering cell treatment agents, nanorobots, and macrophage robots), and other types of microrobots.

In accordance with an aspect of the present disclosure, a bed-integrated electromagnetic field apparatus includes a first electromagnet, one or more second electromagnets disposed to have a predetermined angle with the first electromagnet, and a bed including the first electromagnet and the second electromagnets.

In the present disclosure, the first electromagnet may be a solenoid, or a circular, quadrangular, or saddle-type coil.

In the present disclosure, the first electromagnet may be of a soft-ferrite core or air-core type.

The term "circular electromagnet" as used herein refers to a ring-shaped magnet, that is, an endless magnet having no end demagnetizing affect.

In the present disclosure, the first electromagnet may be configured to produce a magnetic field in a z-axis direction.

The term "z-axis" as used herein refers to an axis which is parallel to the center axis of the first electromagnet, which is perpendicular to the longitudinal direction of the bed, and which is oriented upwards.

In the present disclosure, the second electromagnet may be a solenoid, or a circular, quadrangular, or saddle-type coil.

In the present disclosure, the second electromagnet may be of a soft-ferrite core or air-core type.

In the present disclosure, the second electromagnet may be configured to produce a magnetic field in x-axis and y-axis directions.

The term "x-axis" as used herein refers to an axis which is parallel to the center axis of the first electromagnet, and which is parallel to the longitudinal direction of the bed.

The term "y-axis" as used herein refers to an axis which is perpendicular to the center axis of the first electromagnet, which is perpendicular to the longitudinal direction of the bed, and which is perpendicular both to the x-axis and to the z-axis.

In an embodiment of the present disclosure, the first electromagnet may include a first support plate disposed on one side thereof, a second support plate disposed opposite the first support plate, a central part configured to connect the first support plate and the second support plate through a connection part, and a first winding wound along a circumference of the central part.

According to the present disclosure, the central part of the first electromagnet may have a hollow part formed therein, but is not limited thereto.

According to the present disclosure, the connection part may connect each of the first support plate and the second support plate to the central part, and the one or more second electromagnets may contact the first electromagnet so as to form a predetermined angle.

According to the present disclosure, the connection part may further include a groove part for facilitating connection with the second electromagnet, but is not limited thereto.

In an embodiment of the present disclosure, at least one of the first support plate, the second support plate, the connection part, or the central part may be made of one or more materials selected from a group consisting of Fe—Co based alloy, aluminum, pure iron, iron nitride, electron steel containing bismuth, and a combination thereof, but the materials are not limited thereto.

In an embodiment of the present disclosure, the first winding may include a conductive metal such as enamel, copper, or aluminum, but is not limited thereto.

In an embodiment of the present disclosure, one or more second electromagnets may include a core part. The core part may include a lower surface disposed to have a predetermined angle with the first electromagnet and an upper surface disposed opposite the lower surface. The second electromagnets may include a second winding wound between the upper surface and the lower surface.

In an embodiment of the present disclosure, the number of second electrodes may be two.

In an embodiment of the present disclosure, the upper surface may be disposed to face the center axis of the first electromagnet.

In an embodiment of the present disclosure, the one or more second electromagnets may be disposed to be opposite to each other.

The lower surface of the one or more second electromagnets according to the present disclosure may be disposed to form an angle of 0-90°, 0-80°, 0-75°, 0-70°, 0-65°, 0-50°, 0-45°, 0-40°, 30-60°, 30-50°, or 35-45° (for example, 0-45°) with the support plate of the first electromagnet or with the connection part of the first electromagnet, but is not limited thereto.

In an embodiment of the present disclosure, the second wiring may include a conductive metal such as enamel, copper, or aluminum, but is not limited thereto.

In an embodiment of the present disclosure, the core part may be made of one or more materials selected from a group consisting of Fe—Co based alloy, aluminum, pure iron, iron nitride, electron steel containing bismuth, and a combination thereof, but the materials are not limited thereto.

In an embodiment of the present disclosure, the bed may include one or more curved parts and a support part disposed between the one or more curved parts.

In an embodiment of the present disclosure, the curvature of the curved part may be formed in a shape corresponding to an angle at which the second coil is disposed.

In an embodiment of the present disclosure, the first electromagnet and one or more second electromagnets may be disposed inside the bed.

In an embodiment of the present disclosure, the bed may further include a power supply unit for supplying power to the first and second electromagnets.

In the present disclosure, the power supply unit may be disposed inside the bed.

In an embodiment of the present disclosure, the bed may further include a movement unit for linearly moving the first electromagnet and second electromagnets.

In an embodiment of the present disclosure, the bed may further include a cooling unit for cooling down heat generated by the first electromagnet, the second electromagnet, the bed, the power supply unit, or the movement unit.

In the present disclosure, the cooling unit may be disposed inside the bed.

In an embodiment of the present disclosure, the apparatus may further include a microrobot including a magnetic substance.

The microrobot 300 according to the present disclosure may be implemented in a wired or wireless manner.

The microrobot according to the present disclosure may further include at least one element selected from a group consisting of a camera module, a position information provision unit, a driving unit, a treatment unit, a robot control unit, a data transmission/reception unit, and a wireless power reception unit.

In an embodiment of the present disclosure, the apparatus may include: a first electromagnet including a first support plate disposed on one side thereof, a second support plate disposed opposite the first support plate, a central part configured to connect the first support plate and the second support plate through a connection part, and a first winding wound along a circumference of the central part; one or more second electromagnets, each including a core part having a lower surface disposed to have a predetermined angle with the first electromagnet and an upper surface disposed opposite the lower surface, and a second winding wound between the upper surface and the lower surface; and a bed which includes one or more curved parts and a support part disposed between the one or more curved parts, and in which the first electromagnet and the one or more second electromagnets are disposed.

In accordance with another aspect of the present disclosure, a method for driving a microrobot includes an application operation of applying an electric current to an electromagnetic field apparatus including one or more electromagnets so as to generate an electromagnetic field.

The method for driving a microrobot according to the present disclosure includes the same elements as those of the bed-integrated electromagnetic field apparatus described above, and repeated descriptions thereof will be omitted to avoid making this specification excessively complicated.

In an embodiment of the present disclosure, the application operation may further include an operation of applying currents in different directions to one or more electromagnets.

In an embodiment of the present disclosure, the method may further include an adjustment operation of adjusting the position of the microrobot by adjusting the intensity or direction of electric currents applied to the first and second electromagnets.

Advantageous Effects

The present disclosure relates to a bed-integrated electromagnetic field apparatus for the controlling the movement of a microrobot, and a method for driving a microrobot by using the same. The bed-integrated electromagnetic field apparatus according to the present disclosure is advantageous in that the same can accurately control the movement of a medical device that can be inserted into a human body (for example, a microrobot), and the apparatus can be made compact and thus can be used for a surgery for diagnosing and treating a blood vessel disease or the like.

BEST MODE FOR CARRYING OUT THE INVENTION

A bed-integrated electromagnetic field apparatus includes: a first electromagnet including a first support plate disposed on one side thereof, a second support plate disposed opposite the first support plate, a central part for connecting the first support plate and the second support plate through a connection part, and a first winding wound along a circumference of the central part; one or more second electromagnets, each including a core part having a lower surface disposed to have a predetermined angle with the first electromagnet and an upper surface disposed opposite the lower surface, and a second winding wound between the upper surface and the lower surface; and a bed which includes one or more curved parts and a support part disposed between the one or more curved parts, and in which the first electromagnet and the one or more second electromagnets are disposed.

DETAILED DESCRIPTION

The above-mentioned aspects, features, and advantageous effects will become clearer from the following detailed description with reference to the accompanying drawings, and a person skilled in the art to which the present disclosure pertains will easily implement the technical idea of the present disclosure. in the following description of the present disclosure, detailed description regarding known arts related to the present disclosure will be omitted if deemed to be likely to unnecessarily obscure the gist of the present disclosure.

Throughout the specification, the description that a part "comprises or includes" an element means that, unless particularly specified otherwise, other elements are not included, but other elements may be further included. The term " . . . part" as used herein refers to a unit for processing at least one function or operation, and may be implemented as hardware, software, or a combination of hardware and software. Moreover, expressions "a/an", "one", and related terms may be used in both singular and plural senses unless otherwise indicated herein in the context of description of the present disclosure or clearly contradicted in the context.

The description that an element is "connected" or "joined" with another element is to be understood that the first element may be directly connected or joined with the second element, but also that another element may exist in the middle. On the other hand, the description that an element is "directly connected" or "directly joined" with another element is to be understood that no other element exists in the middle. Other expressions description relations between elements, such as "between", "immediately between", "adjacent to", or "immediately adjacent to" are also to be interpreted likewise.

Figure 1:
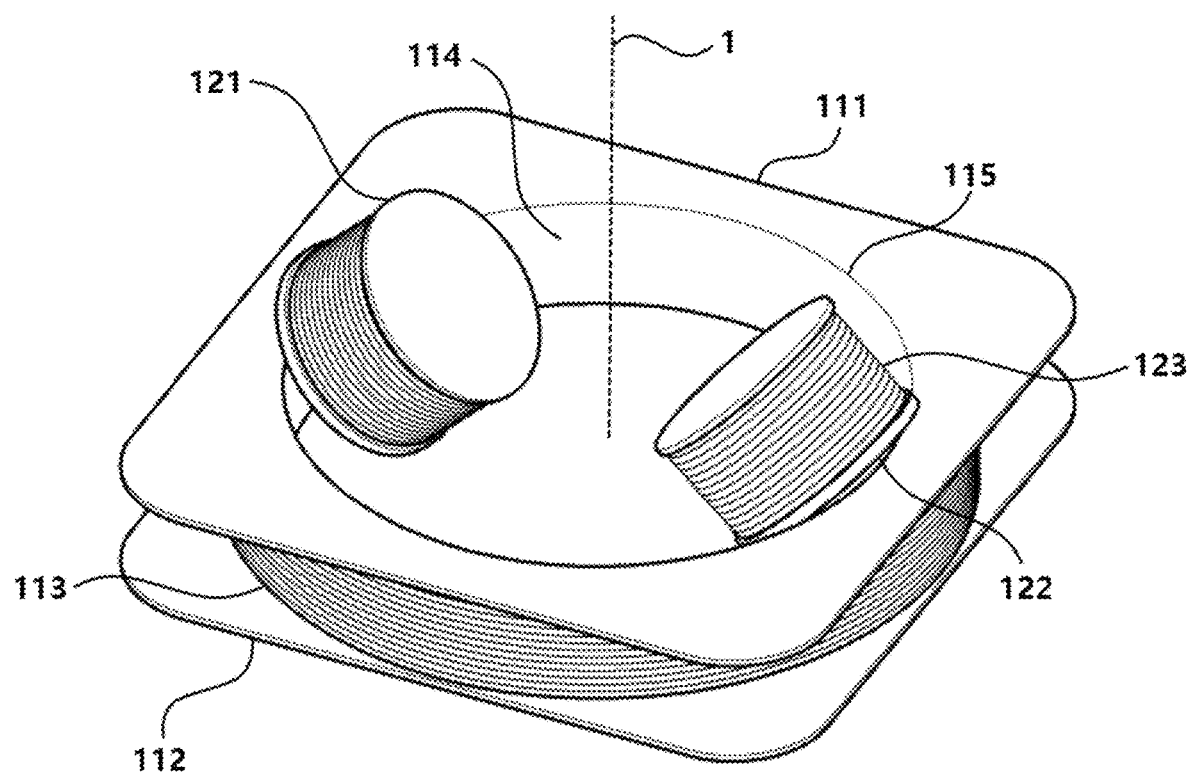
FIG. 1 illustrates an electromagnet module of a bed-integrated electromagnetic field apparatus according to an embodiment of the present disclosure.
Figure 2:
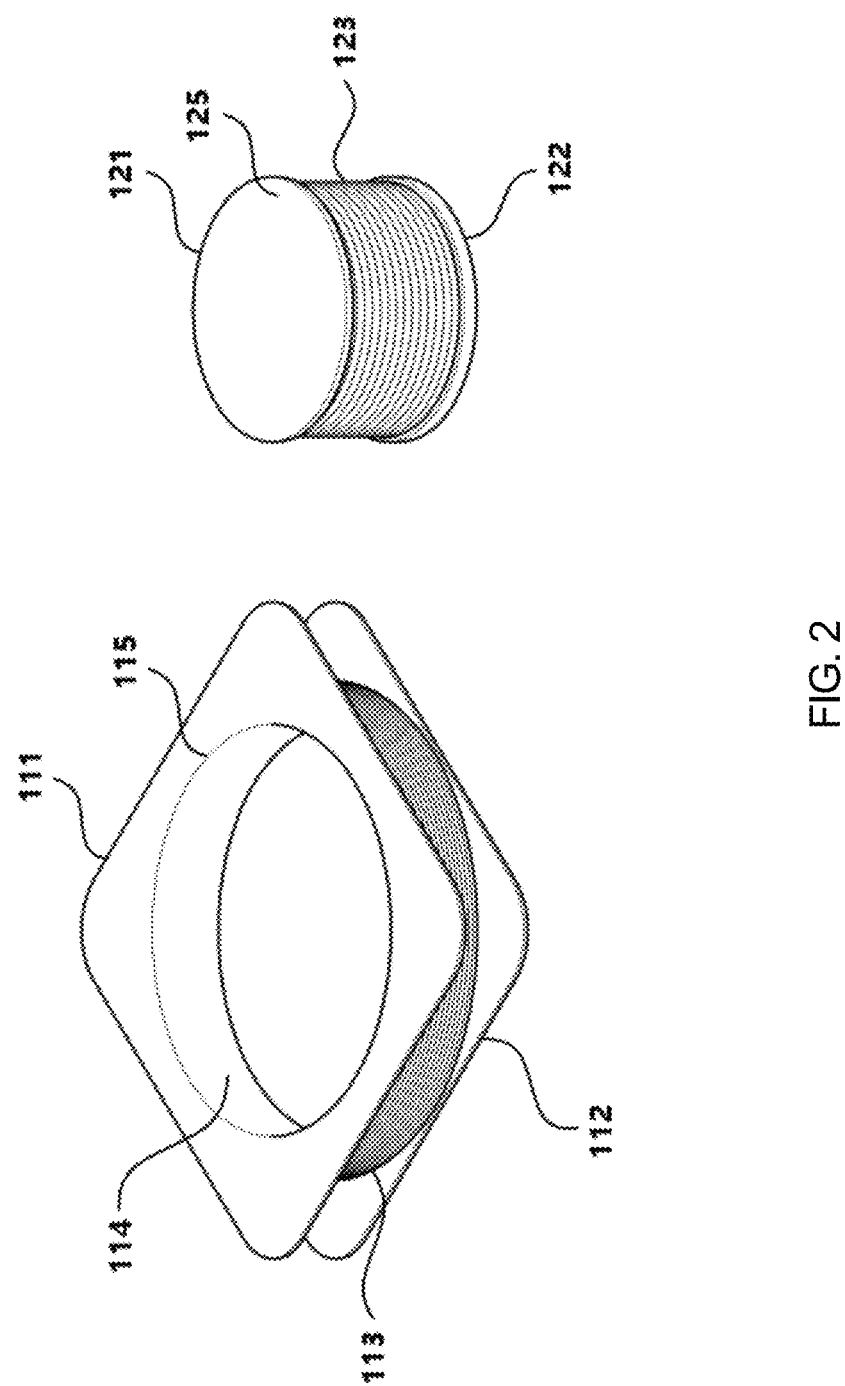
FIG. 2 illustrates a first electromagnet and a second electromagnet of a bed-integrated electromagnetic field apparatus according to an embodiment of the present disclosure.
Figure 3:
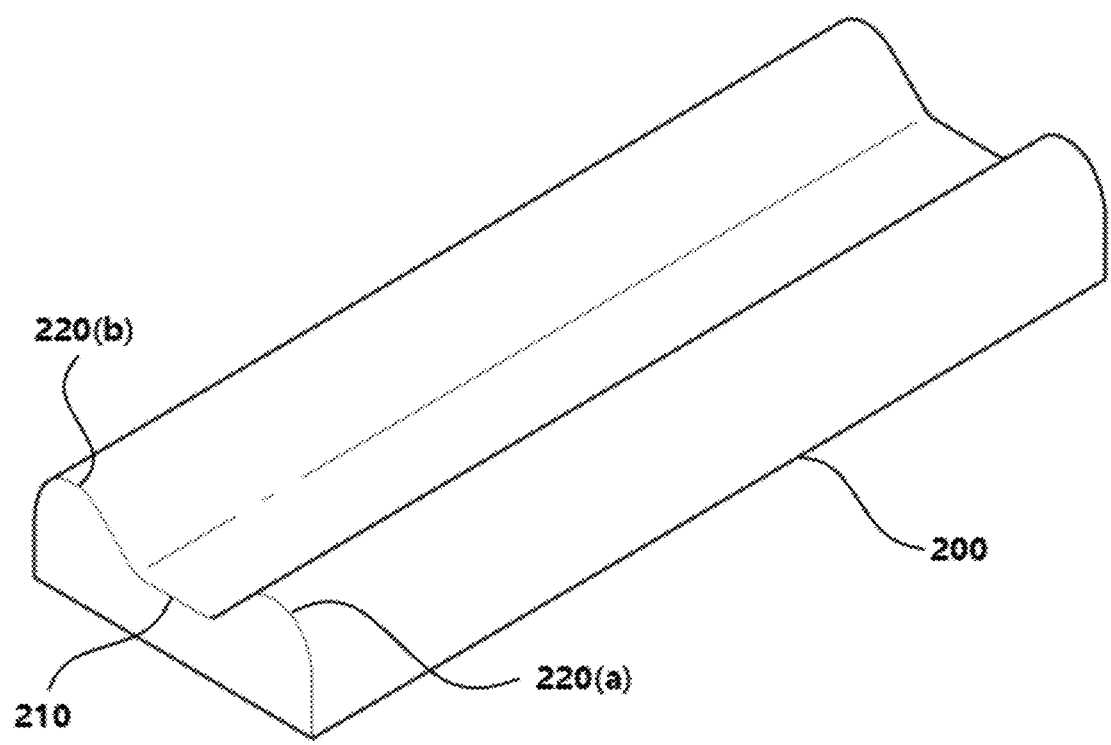
FIG. 3 illustrates a bed of a bed-integrated electromagnetic field apparatus according to an embodiment of the present disclosure.
Figure 4:
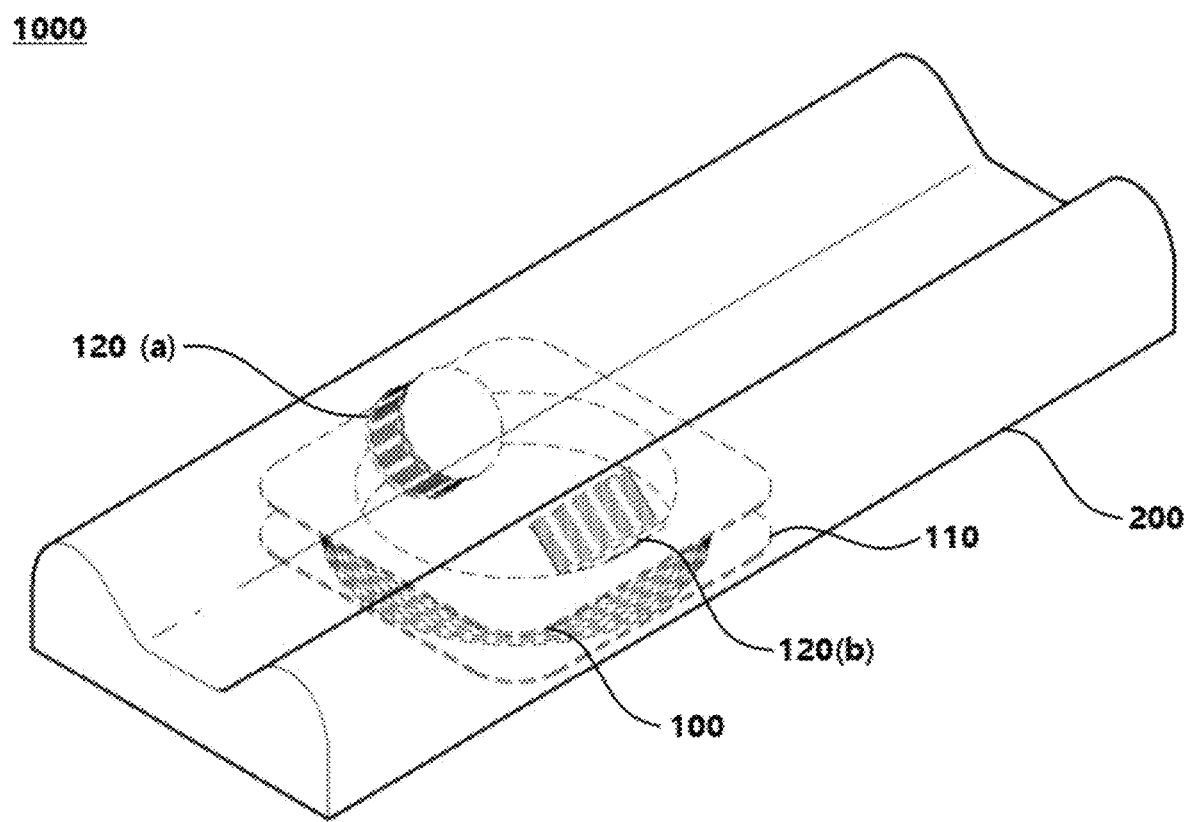
FIG. 4 is a perspective view of a bed-integrated electromagnetic field apparatus according to an embodiment of the present disclosure.

FIG. 1 illustrates an electromagnet module of a bed-integrated electromagnetic field apparatus according to an embodiment of the present disclosure, FIG. 2 illustrates a first electromagnet and a second electromagnet of a bed-integrated electromagnetic field apparatus according to an embodiment of the present disclosure, FIG. 3 illustrates a bed of a bed-integrated electromagnetic field apparatus according to an embodiment of the present disclosure, and FIG. 4 is a perspective view of a bed-integrated electromagnetic field apparatus according to an embodiment of the present disclosure.

Referring to FIGS. 1 to 4, a bed-integrated electromagnetic field apparatus 1000 according to an embodiment may include an electromagnet module 100 and a bed 200, the electromagnet module including a first electromagnet 110 and one or more second electromagnets 120(a) and 120(b) which are disposed to have a predetermined angle with the first electromagnet 110.

As illustrated in FIGS. 1 to 2, the first electromagnet 110 may be a circular electromagnet.

The first electromagnet 110 may include: a first support plate 111 disposed on one side thereof; a second support plate 112 disposed opposite the first support plate 111; a central part 114 for connecting the first support plate 111 and the second support plate 112 through a connection part 115; and a first winding 113 wound along a circumference of the central part 114.

The first support plate 111 is disposed on the top of the first electromagnet 110 so as to support the one or more second electromagnets 120 while being in contact with the one or more second electromagnets 120.

The first support plate 111 may include a groove part (not shown), and accordingly, firmly support the second electromagnets 120 when being connected to the second electromagnets 120.

The second support plate 112 may be flat. The second support plate 112 is disposed below the second electromagnets 120 so as to support the entirety of the electromagnet module 100 while being in contact with the bottom of the bed 200, and the second support plate 112 may firmly support the electromagnet module without changing relative positions of the first electromagnet 110 and the second electromagnets 120 even when the electromagnet module 100 moves.

The connection part 115 may connect the first support plate 111 and the second support plate 112 with the central part 114, and, as illustrated in FIGS. 1 to 4, may have a shape of an edge of a vertically bent portion, but the shape is not limited thereto. For example, the connection part may have a shape of a plane having a predetermined inclination.

On the first support plate 111 or the connection part 115, the one or more second electromagnets 120 may be disposed to have a predetermined angle therewith. The connection part 115 may include a groove part (not shown) which enables the one or more second electromagnets 120 to be coupled thereto, and the one or more second electromagnets 120 may be engaged with the groove of the connection part 115 to be firmly attached to a predetermined position within the electromagnet module 100.

The central part 114 may be connected to the first support plate 111 and the second support plate 112 through the connection part 115, and may be disposed to be perpendicular to each of the first support plate 111 and the second support plate 112.

The central part 114 may form a hollow part within the first electromagnet 110 together with the first support plate 111, the second support plate 112, and the connection part 115. The first electromagnet 110 may form, through the hollow part formed at the center thereof, a space in which the one or more second electromagnets 120 can be disposed, and accordingly, the second electromagnets 120 may be partially disposed within the hollow part and may have a predetermined angle with the first electromagnet 110.

The first electromagnet 110 may include the first winding 113 wound along the circumference of the central part 114.

An electric current supplied from a power supply unit (not shown) disposed within the bed-integrated electromagnetic field apparatus 1000 or the bed 200 may flow through the first winding 113, and, as the central part 114 is disposed in a direction perpendicular to the first support plate 111 and the second support plate 112, the first winding 113 may generate an electromagnetic field in a direction perpendicular to the first support plate 111 and the second support plate 112.

Therefore, as an electric current is applied to the first winding 113 wound around the central part 114, the first electromagnet 110 may generate an electromagnetic field in a vertical direction of the bed 200. For example, in the case of a medical device which is insertable into a human body, a position of a medical device inserted into a human body can be vertically adjusted by a magnet embedded in the medical device such as a microrobot.

The first support plate 111, the second support plate 112, the connection part 115, and the central part 114 of the first electromagnet 110 may be made of one or more materials selected from a group consisting of Fe—Co based alloy, aluminum, pure iron, iron nitride, electron steel containing bismuth, and a combination thereof, but the materials thereof are not limited thereto.

As illustrated in FIGS. 1 to 2, the second electromagnet 120 may be a solenoid electromagnet.

The second electromagnet 120 may include: a core 125 having a lower surface 122 disposed to have a predetermined angle with the first electromagnet 110, and an upper surface 121 disposed opposite the lower surface 122; and a second winding 123 wound between the lower surface 122 and the upper surface 121.

One or more second electromagnets 120 may be included in the bed-integrated electromagnetic field apparatus 1000, and, as illustrated in FIGS. 1 to 4, two second electromagnets may be included in the apparatus.

The lower surface 122 may be disposed to have a predetermined angle with the connection part 115 or the first support plate 111 of the first electromagnet 110. For example, the lower surface is disposed to have an angle of 0 to 45 degrees with the connection part 115 or the first support plate 111 of the first electromagnet 110, so as to optimize the intensity and direction performance of a magnetic field in a longitudinal direction and a widthwise direction of the bed 200 within the same allowable current, and can optimize a three-dimensional magnetic field control performance together with the first electromagnet 110.

In addition, the lower surface 122 may be firmly coupled to the connection part 115 or the first support plate 111 of the first electromagnet 110 through a groove part formed thereon.

The second winding 123 may be wound between the lower surface 122 and the upper surface 121. The second winding 123 may include conductive metal such as enamel, copper, or aluminum.

Meanwhile, as illustrated in FIG. 1, the second electromagnet 120 may be partially positioned in a hollow part formed in the first electromagnet 110, and the second electromagnet 120 may be disposed to be inclined relative to the first electromagnet 110 so as to have a predetermined angle with the first support plate 111 or the connection part 115. Accordingly, the second electromagnet 120 can generate an electromagnetic field in forward, backward, left, and right directions of the bed-integrated electromagnetic field apparatus 1000.

In other words, as illustrated in FIG. 1, the upper surface 121 of the second electromagnet may be disposed to be oriented toward a central axis 1 of the first electromagnet 110, and accordingly, as will be described later, can freely move a medical device which is insertable into a human body in an x-axis direction and a y-axis direction of an electromagnet module.

The bed 200 may include one or more curved parts 220(a) and 220(b), and a support part 210 disposed between the one or more curved parts, and the electromagnet module 100 including the first electromagnet 110 and the second electromagnets 120 may be disposed inside the bed 200.

The support part 210 may be flat to stably support a patient's body.

The bed 200 may further include a power supply unit (not shown) for supplying power to the first electromagnet 110 and the second electromagnets 120.

The bed 200 may further include a movement unit (not shown) for linearly moving the first electromagnet 110 and the second electromagnets 120.

The bed 200 may further include a cooling unit for cooling heat generated from the first electromagnet 110, the second electromagnets 120, the bed 200, the power supply unit, or the movement unit.

Figure 5:
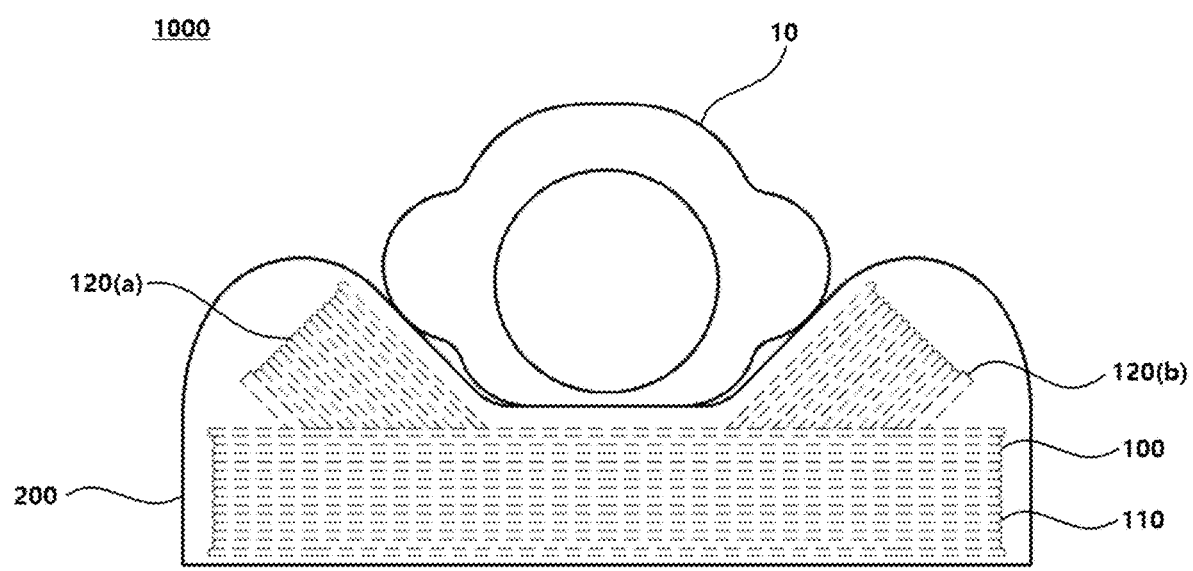
FIG. 5 is a side view of a bed-integrated electromagnetic field apparatus according to an embodiment of the present disclosure.

Referring to FIG. 5, curvatures of the one or more curved parts 220(a) and 220(b) may be formed in a shape corresponding to an angle at which the second electromagnets 120 are disposed. Therefore, the support part 210 and the curved parts 220(a) and 220(b) of the bed 200 may be formed in a shape corresponding to an outward form of the electromagnet module 100, and accordingly, a distance between each of the first electromagnet 110 and the second electromagnets 120, and a patient's body 10 positioned on the bed 200 can become closer.

A distance between a medical device inserted into a patient's body, and each of the first electromagnet 110 and the second electromagnets 120 is remarkably decreased due to the shape of the bed 200, which corresponds to the electromagnet module 100, so that an amount of electric current, which is required for an electromagnet to move a medical device which is insertable into a human body, can be reduced, and accordingly, the medical device can be driven without high power consumption.

Figure 6:
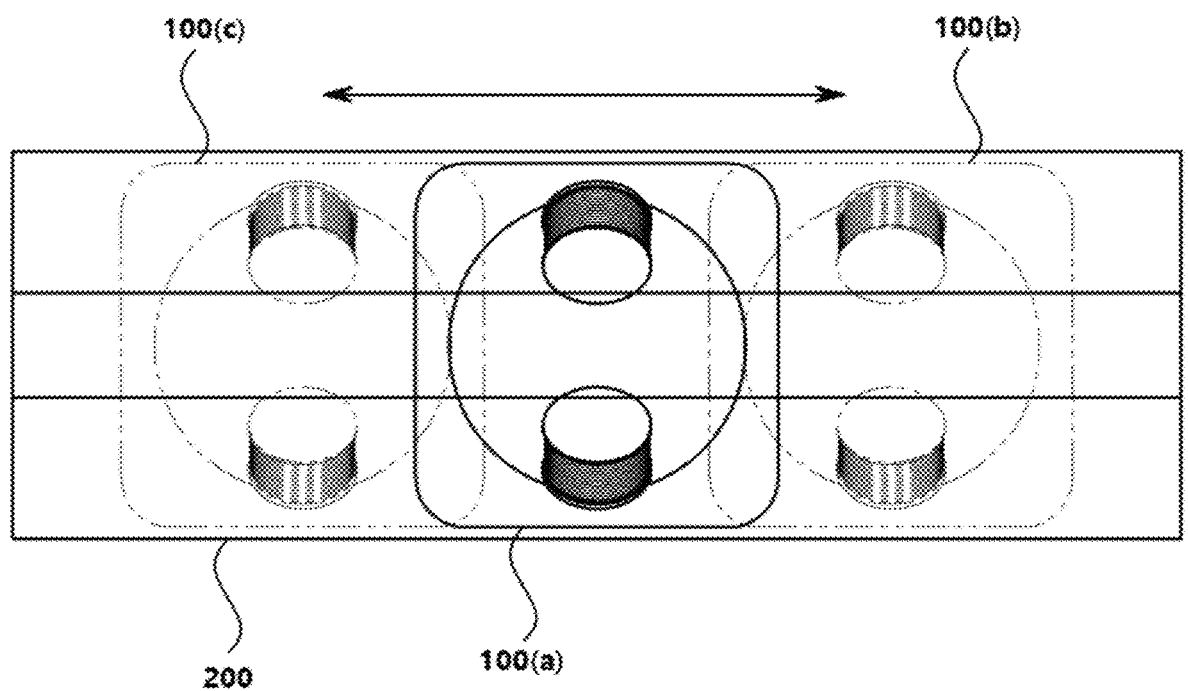
FIG. 6 illustrates linear movement of an electromagnet module in a bed-integrated electromagnetic field apparatus according to an embodiment of the present disclosure.

FIG. 6 illustrates linear movement of an electromagnet module in a bed-integrated electromagnetic field apparatus according to an embodiment of the present disclosure.

Referring to FIG. 6, the electromagnet module 100 may linearly move to arbitrary positions 100(a), 100(b), and 100(c) of the bed by means of motor driving of a movement unit (not shown) included in the bed 200 or the electromagnetic field apparatus 1000.

The bed-integrated electromagnetic field apparatus 1000 according to an embodiment can move the electromagnet module 100 to a position where a disease has occurred or the occurrence of a disease is suspected in the body of a patient positioned on the bed 200, and can move a medical device, which is insertable into a human body, to a corresponding section by means of the electromagnet module 100 which induces the medical device to the corresponding position.

Therefore, the bed-integrated electromagnetic field apparatus 1000 according to an embodiment can freely control a position of a medical device inserted into a patient's body by means of linear movement of the electromagnet module 100.

Figure 7A:
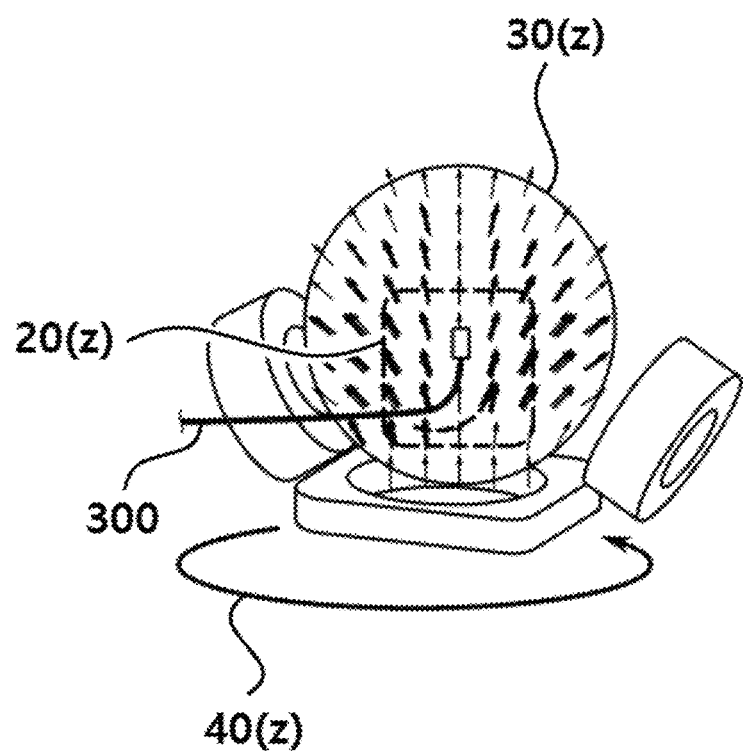
FIG. 7A illustrates generation of an electromagnetic field in a z-axis direction of a bed-integrated electromagnetic field apparatus according to an embodiment of the present disclosure.
Figure 7B:
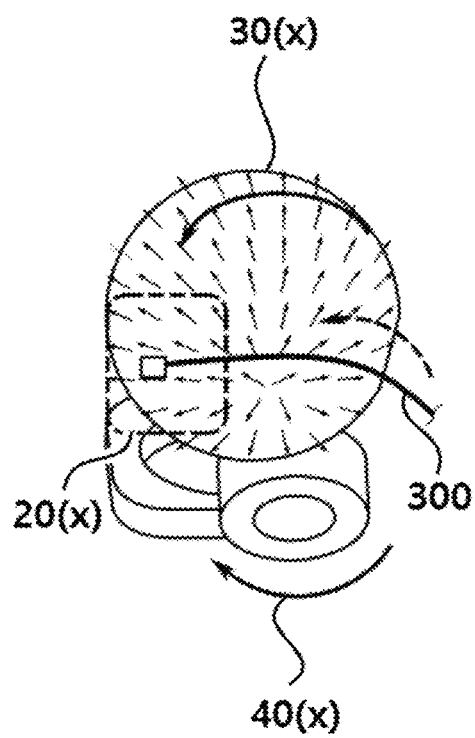
FIG. 7B illustrates generation of an electromagnetic field in an x-axis direction of a bed-integrated electromagnetic field apparatus according to an embodiment of the present disclosure.
Figure 7C:
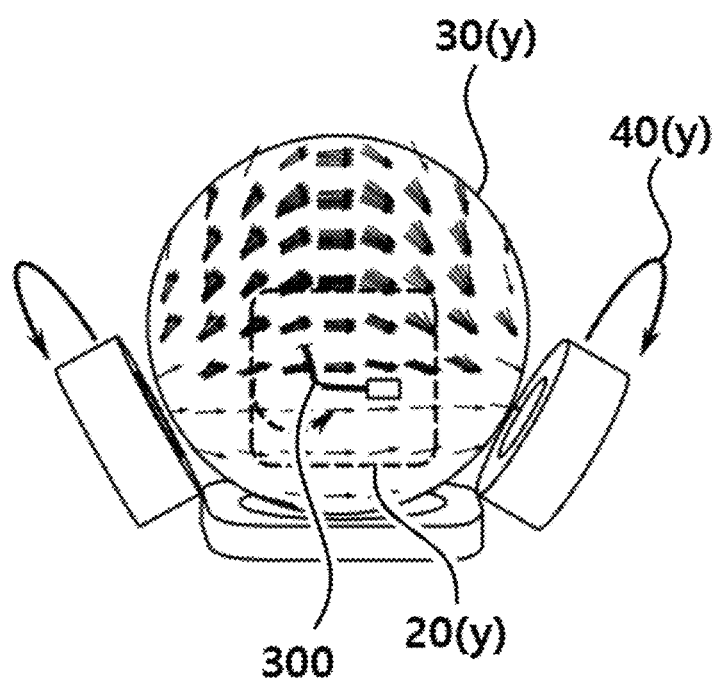
FIG. 7C illustrates generation of an electromagnetic field in a y-axis direction of a bed-integrated electromagnetic field apparatus according to an embodiment of the present disclosure.

FIG. 7A illustrates generation of an electromagnetic field in a z-axis direction of a bed-integrated electromagnetic field apparatus according to an embodiment of the present disclosure, FIG. 7B illustrates generation of an electromagnetic field in an x-axis direction of a bed-integrated electromagnetic field apparatus according to an embodiment of the present disclosure, and FIG. 7C illustrates generation of an electromagnetic field in a y-axis direction of a bed-integrated electromagnetic field apparatus according to an embodiment of the present disclosure.

Referring to FIGS. 7A to 7C, a bed-integrated electromagnetic field apparatus according to an embodiment may move a microrobot 300 to an area of interest by focusing a magnetic field by means of a first electromagnet and a second electromagnet.

Specifically, as illustrated in FIG. 7A, a user can move the microrobot 300 in a z-axis direction by applying an electric current to a first electromagnet. The user can freely move the microrobot 300 in the z-axis direction of an area of interest 20(z) by adjusting the direction and intensity 40(z) of the electric current applied to the first electromagnet, and accordingly, the user can properly drive the microrobot 300 in the z-axis direction within the area of interest 20(z) of a patient's body.

As illustrated in FIGS. 7B and 7C, the user can move the microrobot 300 in an x-axis direction and a y-axis direction by applying an electric current to a second electromagnet. As described above, an upper surface of the second electromagnet may be disposed to be oriented toward a central axis 1 of the first electromagnet, and a lower surface thereof may be disposed to have a predetermined angle with a first support plate or a connection part of the first electromagnet, so that the second electromagnet can move the microrobot 300 in an x-axis direction and a y-axis direction of an electromagnet module. As described above for the movement in the z-axis direction, in regard to the movement of the microrobot 300 in the x-axis and y-axis directions, the user can freely move the microrobot 300 within areas of interest 20(x) and 20(y) by moving the microrobot 300 in the x-axis and y-axis directions by means of adjustment of the direction and intensity 40(x) and 40(y) of the electric current applied to the second electromagnet.

The user can apply electric currents of opposite directions to the second electromagnets, and accordingly, can increase the intensities of magnetic fields 30(x) and 30(y) generated in an area of interest by focusing the magnetic fields.

The user can freely and precisely move a microrobot in an area of interest by adjusting each of the direction and intensity of the electric current applied to the first electromagnet and the second electromagnet and thus overlapping the areas of interest 20(x), 20(y), and 20(z) inside a patient's body and the respective magnetic fields 30(x), 30(y), and 30(z) generated by the first and second electromagnets. As specific arrangement forms of the first and second electromagnets and the direction and intensity of the electric current applied to each of the electromagnets can be independently adjusted, the microrobot 300 can be accurately driven.

Figure 8:
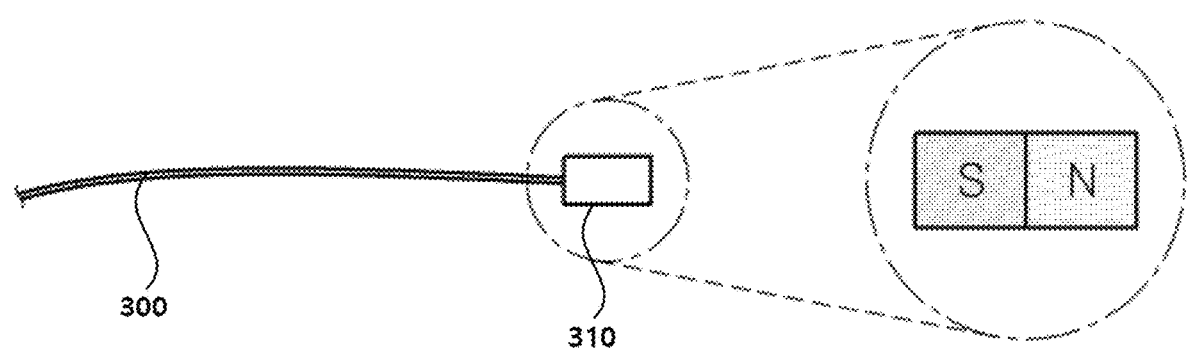
FIG. 8 illustrates a microrobot of a bed-integrated electromagnetic field apparatus according to an embodiment of the present disclosure.

FIG. 8 illustrates a microrobot of a bed-integrated electromagnetic field apparatus according to an embodiment of the present disclosure.

Referring to FIG. 8, the microrobot 300 may include a magnet so as to have an arbitrary magnetization direction. The microrobot 300 may rotate and/or move in an arbitrary direction by means of a magnetic field generated by the bed-integrated electromagnetic field apparatus described above.

The microrobot 300 may be implemented in a wired manner or a wireless manner.

The microrobot 300 may include a robot body. The microrobot 300 may be constituted only by a robot body 310, or may further include at least one element selected from a group consisting of a camera module, a position information provision unit, a driving unit, a treatment unit, a robot control unit, a data transmission/reception unit, and a wireless power reception unit.

The robot body 310 is a part for defining the outside of the microrobot 300, and may be manufactured to have a size which allows the microrobot to move inside a subject or through a blood vessel. In addition, a leading portion of the robot body 310 may be manufactured to be streamlined so as to reduce friction with a bloodstream, the leading portion of the robot body 310 may include a residue collector and the like, and the residue collector collects treatment residue generated during treatment of a blood vessel.

Figure 9:
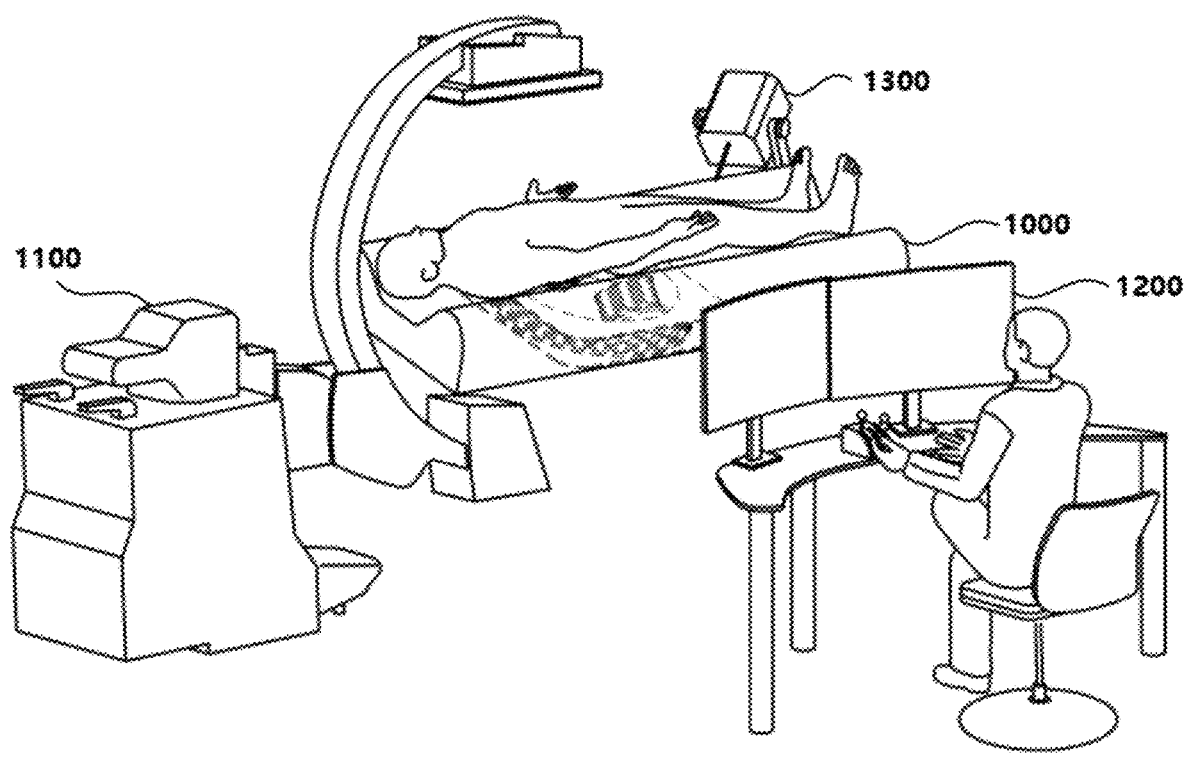
FIG. 9 illustrates usage of a bed-integrated electromagnetic field apparatus according to an embodiment of the present disclosure, the usage being associated with a medical device such as an X-ray device.

FIG. 9 illustrates usage of a bed-integrated electromagnetic field apparatus according to an embodiment of the present disclosure, the usage being associated with a medical device such as an X-ray device.

Referring to FIG. 9, a bed-integrated electromagnetic field apparatus 1000 according to an embodiment may be used in conjunction with an X-ray device 1100, an image navigation system 1200, and a catheter insertion/collection device 1300 in a hospital.

Figure 10:
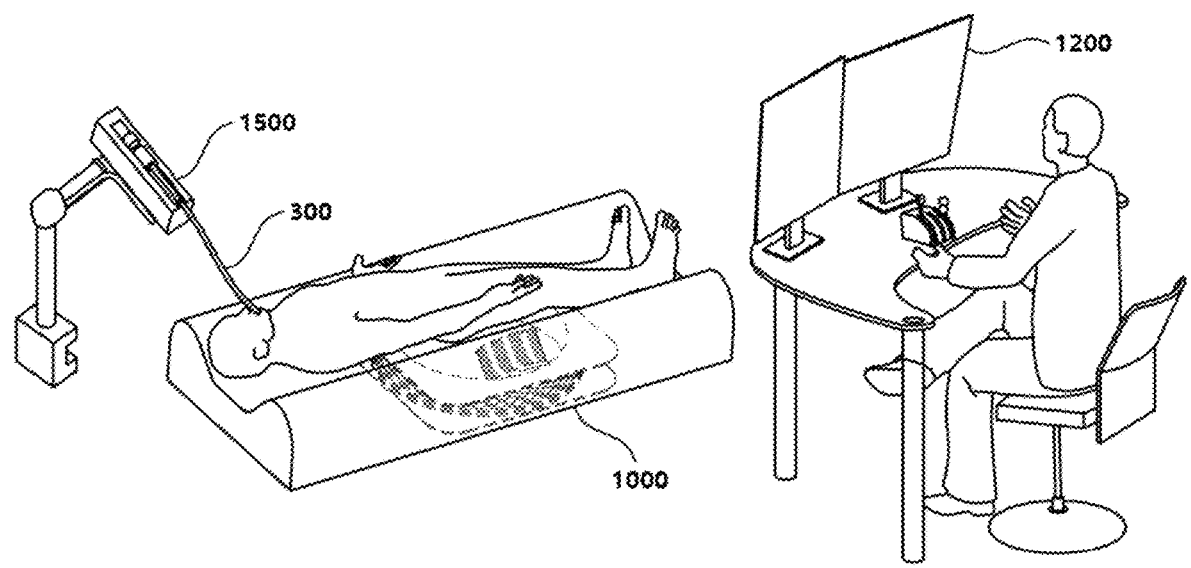
FIG. 10 illustrates usage of a bed-integrated electromagnetic field apparatus according to an embodiment of the present disclosure, the usage being associated with a medical device such as a microrobot induction device.

FIG. 10 illustrates usage of a bed-integrated electromagnetic field apparatus according to an embodiment of the present disclosure, the usage being associated with a medical device such as a microrobot induction device.

Referring to FIG. 10, the bed-integrated electromagnetic field apparatus 1000 according to an embodiment may be used in conjunction with a microrobot induction device 1500 and an image navigation system 1200 in a hospital.

Therefore, as illustrated in FIG. 9, the bed-integrated electromagnetic field apparatus 1000 may be implemented by using the microrobot 300 functioning as a blood vessel robot in conjunction with the catheter insertion/collection device 1300, or as illustrated in FIG. 10, may be implemented by using the microrobot 300 functioning as a wired digestive system endoscope in conjunction with the microrobot induction device 1500.

As described above, the number of coils included in the bed-integrated electromagnetic field apparatus 1000 according to an embodiment is minimized, and the bed-integrated electromagnetic field apparatus has a structure integrated with a bed on which a patient's body is positioned, thereby enabling reduction of the entire size of a system.

Accordingly, a bed-integrated electromagnetic field apparatus can be excellently compatible with an existing medical device, be easily installed in a hospital, and easily perform a medical procedure because there is no interference with the medical procedure, which is incurred due to an electromagnetic field system.

The present disclosure described above can be replaced, modified, and changed in other forms, without departing from the technical idea of the present disclosure, by a person having common knowledge in the technical field to which the present disclosure belongs, and is thus not limited to the embodiments described above and following drawings.

DESCRIPTION OF REFERENCE NUMBERS

100: Electromagnet module
110: First electromagnet
111: First support plate
112: Second support plate
113: First winding
114: Central part
115: Connection part
120: Second electromagnet
121: Upper surface
122: Lower surface
123: Second winding
125: Core part
200: Bed
210: Support part
220: Curved part

INDUSTRIAL APPLICABILITY

The present disclosure relates to a bed-integrated electromagnetic field apparatus for controlling the movement of a microrobot, and a method for driving a microrobot by using the same and, more specifically, to an electromagnetic field apparatus which can accurately control the movement of a microrobot, and which can be made compact and thus has excellent compatibility with other medical equipment.

What is claimed is:

1. A bed-integrated electromagnetic field apparatus comprising:
   a first electromagnet including a first support plate disposed on one side thereof, a second support plate disposed opposite the first support plate, a central part configured to connect the first support plate and the second support plate through a connection part, and a first winding wound along a circumference of the central part;
   one or more second electromagnets, each including a core part having a lower surface disposed to have a predetermined angle with the first electromagnet and an upper surface disposed opposite the lower surface, and a second winding wound between the upper surface and the lower surface; and
   a bed which includes one or more curved parts and a support part disposed between the one or more curved parts, and in which the first electromagnet and the one or more second electromagnets are disposed.

2. The bed-integrated electromagnetic field apparatus of claim 1, wherein the central part includes a hollow part formed therein.

3. The bed-integrated electromagnetic field apparatus of claim 1, wherein the lower surface is disposed to be in contact with the connection part.

4. The bed-integrated electromagnetic field apparatus of claim 1, wherein curvatures of the curved parts are formed in a shape corresponding to an angle at which the second coil is disposed.

5. The bed-integrated electromagnetic field apparatus of claim 1, further comprising a power supply unit.

6. The bed-integrated electromagnetic field apparatus of claim 1, further comprising a cooling unit.

7. The bed-integrated electromagnetic field apparatus of claim 1, wherein each of the second electromagnets is disposed to be oriented toward a central axis of the first electromagnet, and the second electromagnets are disposed to be opposite to each other.

8. The bed-integrated electromagnetic field apparatus of claim 1, further comprising a microrobot including a magnetic substance.

9. The bed-integrated electromagnetic field apparatus of claim 1, wherein the lower surface of the second electromagnet is disposed to have an angle of 0 to 45 degrees with the connection part.

10. A method for driving a microrobot, the method comprising an electric current application operation of applying an electric current to an electromagnetic field apparatus including one or more electromagnets so as to generate an electromagnetic field,
    wherein the electromagnetic field apparatus comprises:
    a first electromagnet including a first support plate disposed on one side thereof, a second support plate disposed opposite the first support plate, a central part configured to connect the first support plate and the second support plate through a connection part, and a first winding wound along a circumference of the central part;
    one or more second electromagnets, each including a core part having a lower surface disposed to have a predetermined angle with the first electromagnet and an upper surface disposed opposite the lower surface, and a second winding wound between the upper surface and the lower surface; and
    a bed which includes one or more curved parts and a support part disposed between the one or more curved parts, and in which the first electromagnet and the one or more second electromagnets are disposed.

11. The method of claim 10, wherein the lower surface of the second electromagnet is disposed to have an angle of 0 to 45 degrees with the connection part.

12. The method of claim 10, wherein the number of the second electromagnets is two, and electric currents of opposite directions are applied to the second electromagnets, respectively.

13. The method of claim 10, further comprising an adjustment operation of adjusting a position of a microrobot by adjusting an intensity or a direction of an electric current applied to each of the first electromagnet and the second electromagnets.

* * * * *